United States Patent
Soni et al.

(10) Patent No.: US 7,132,444 B2
(45) Date of Patent: Nov. 7, 2006

(54) PROCESS FOR THE PREPARATION OF TRANS-3-ETHYL-2,5-DIHYDRO-4-METHYL-N-[2-[4-[[[[(4-METHYL CYCLOHEXYL) AMINO]CARBONYL]AMINO]SULFONYL]PHENYL]ETHYL]-2-OXO-1H-PYRROLE-1-CARBOXAMIDE

(75) Inventors: Rohit Ravikant Soni, Baroda (IN); Thennati Rajamannar, Baroda (IN); Rajeev Budhdev Rehani, Baroda (IN)

(73) Assignee: Sun Pharmaceutical Industries, Ltd., Mumbai (IN)

(*) Notice: Subject to any disclaimer, the term of this patent is extended or adjusted under 35 U.S.C. 154(b) by 268 days.

(21) Appl. No.: 10/501,743

(22) PCT Filed: Jan. 6, 2003

(86) PCT No.: PCT/IN03/00004

§ 371 (c)(1),
(2), (4) Date: Jun. 30, 2004

(87) PCT Pub. No.: WO03/057131

PCT Pub. Date: Jul. 17, 2003

(65) Prior Publication Data

US 2005/0070593 A1 Mar. 31, 2005

(30) Foreign Application Priority Data

Jan. 7, 2002 (IN) .............................. 9/MUM/2002

(51) Int. Cl.
*A61K 31/40* (2006.01)
*C07D 207/00* (2006.01)

(52) U.S. Cl. .................. 514/423; 514/424; 548/530
(58) Field of Classification Search ................ 514/423, 514/424; 548/530

See application file for complete search history.

(56) References Cited

U.S. PATENT DOCUMENTS 4,379,785 A * 4/1983 Weyer et al. ............... 514/183
5,264,449 A * 11/1993 Albaugh .................... 514/397

* cited by examiner

*Primary Examiner*—Joseph K. McKane
*Assistant Examiner*—Susannah L. Chung
(74) *Attorney, Agent, or Firm*—Pharmaceutical Patent Attorneys, LLC

(57) ABSTRACT

The present invention provides a novel process for preparation of trans-3-ethyl 2,5-dihydro-4-methyl-N-[2-[4-[[[[(4-methyl cyclohexyl)amino]carbonyl]amino]sulfonyl]phenyl]ethyl]-2-oxo-1H-pyrrole-1-carboxamide via the novel intermediate compounds of formula 3.

18 Claims, No Drawings

PROCESS FOR THE PREPARATION OF TRANS-3-ETHYL-2,5-DIHYDRO-4-METHYL-N-[2-[4-[[[[(4-METHYL CYCLOHEXYL) AMINO]CARBONYL]AMINO]SULFONYL] PHENYL]ETHYL]-2-OXO-1H-PYRROLE-1-CARBOXAMIDE

The present invention relates to a novel process for the preparation of trans-3-Ethyl-2,5-dihydro-4-methyl-N-[2-[4-[[[[(4-methyl cyclohexyl)amino]carbonyl]amino]sulfonyl] phenyl]ethyl]-2-oxo-1H-pyrrole-1-carboxamide, commonly known as glimepiride (INN Name), a compound of Formula 1. Trans-3-Ethyl-2,5-dihydro-4-methyl-N-[2-[4-[[[[(4-methylcyclohexyl)amino]carbonyl]amino]sulfonyl]phenyl] ethyl]-2-oxo-1H-pyrrole-1-carboxamide is useful in the treatment of diabetes mellitus.

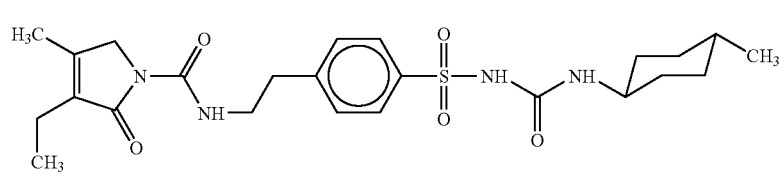

Formula 1

U.S. Pat. No. 4,379,785 (hereinafter referred to as the '785 patent) discloses heterocyclic substituted sulfonylureas, particularly N-[4-[2-(3-ethyl-4-methyl-2-oxo-3-pyrroline-1-carboxamido)-ethyl]-benzenesulfonyl]-N'-4-methylcyclohexylurea i.e. glimepiride. The '785 patent teaches the preparation of glimepiride starting from 3-Ethyl-4-methyl-3-pyrrolidin-2-one and 2-phenylethylisocyanate to give [2-(3-Ethyl-4-methyl-2-carbonyl pyrrolidine amido)ethyl] benzene. The [2-(3-Ethyl-4-methyl-2-carbonyl pyrrolidine amido)ethyl]benzene is converted to the 4-[2-(3-Ethyl-4-methyl-2-carbonyl pyrrolidine amido)ethyl]benzene sulfonamide, a compound of formula 4, by reacting with chlorosulfonic acid, followed by treatment with ammonia solution. This intermediate compound of formula 4 is further reacted with trans-4-methylcyclohexyl isocyanate to form glimepiride. The '785 patent teaches a three step process for preparation of the intermediate compound of formula 4, i.e. 4-[2-(3-Ethyl-4-methyl-2-carbonyl pyrrolidine amido)ethyl] benzene sulfonamide, which is represented in Scheme 1.

Scheme1

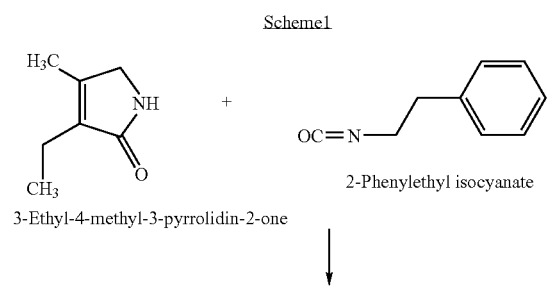

3-Ethyl-4-methyl-3-pyrrolidin-2-one        2-Phenylethyl isocyanate

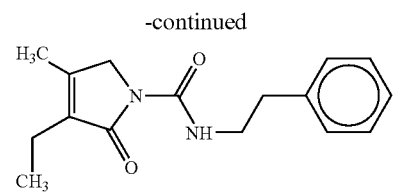

[2-(3-Ethyl-4-methyl-2-carbonyl pyrrolidine amido)ethyl]benzene

↓ Chlorosulfonic acid

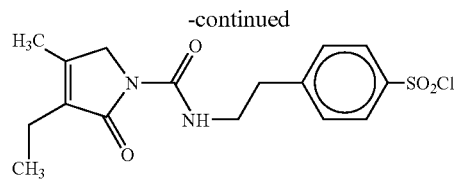

4-[2-(3-Ethyl-4-methyl-2-carbonyl pyrrolidine amido)ethyl]benzene sulfonylchloride ↓ Ammonia solution

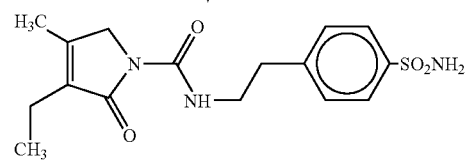

4-[2-(3-Ethyl-4-methyl-2-carbonyl pyrrolidine amido)ethyl]benzene sulfonylchloride Formula 4

As this intermediate compound of formula 4 is further converted to glimepiride in a one step reaction, the purity of glimepiride would be greatly affected by the purity of the intermediate compound of formula 4. When the intermediate compound of formula 4, was prepared by the process of the '785 patent, we found that the purity of this intermediate does not exceed 95–96%.

OBJECTIVES OF THE INVENTION

The objective of the present invention is to prepare the intermediate compound of formula 4, viz., 4-[2-(3-Ethyl-4-methyl-2-Carbonyl pyrrolidine amido)ethyl]benzene sulfonamide of higher purity.

A further objective of the present invention is to prepare the intermediate compound of formula 4, viz., 4-[2-(3-Ethyl-4-methyl-2-carbonyl pyrrolidine amido)ethyl]benzene sulfonamide to obtain the desired quality product by a cost effective process.

Yet another objective of the present invention is to prepare trans-3-ethyl 2,5-dihydro-4-methyl-N-[2-[4-[[[[(4-methyl cyclohexyl)amino]carbonyl]amino]sulfonyl]phenyl]ethyl]-2-oxo-1H-pyrrole-1-carboxamide, i.e. glimepiride of pharmaceutically acceptable quality, by employing the intermediate compound of formula 4, viz., 4-[2-(3-Ethyl-4-methyl-2-carbonyl pyrrolidine amido)ethyl]benzene sulfonamide, that is prepared by the process of the present invention.

SUMMARY OF THE INVENTION

The present invention provides a process the preparation of trans-3-Ethyl-2,5-dihydro-4-methyl-N-[2-[4-[[[[(4-methylcyclohexyl)amino]carbonyl]amino]sulfonyl]phenyl]ethyl]-2-oxo-1H-pyrrole-1-carboxamide, a compound of the formula 1,

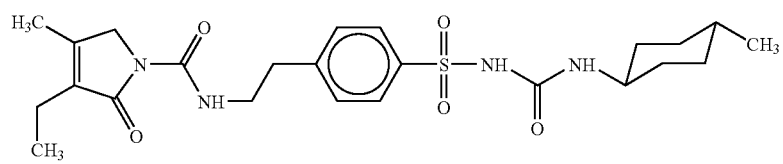

Formula 1 comprising, a) reacting 3-Ethyl-4-methyl-3-pyrrolidin-2-one with a compound of formula 2,

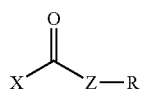

Formula 2 to obtain a compound of formula 3,

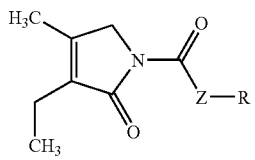

Formula 3 b) reacting a compound of formula 3 with 4-(2-Aminoethyl)benzene sulfonamide to obtain 4-[2-(3-Ethyl-4-methyl-2-carbonyl pyrrolidine amido)ethyl]benzene sulfonamide, a compound of formula 4,

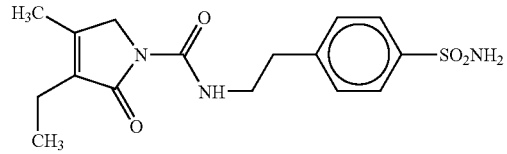

Formula 4 c) and further reacting the compound of formula 4 with trans-4-methylcyclohexyl isocyanate to obtain the compound of formula 1, wherein, X is halogen, nitroaryl or haloaryl, Z is O, S or NY, wherein Y is $C_1$–$C_5$-alkyl, $C_1$–$C_5$-haloalkyl, aryl or aralkyl, and R is aryl or heteroaryl, where aryl or hetroaryl radical is unsubstituted or substituted by one or more radicals from the group consisting of nitro, halogen, cyano, azido, haloalkyl, CO—$R^1$, $SR^2$, SO—$R^3$ and $SO_2$—$R^4$, $R^1$ is H, $C_1$–$C_5$-alkyl, $C_2$–$C_5$-alkenyl, $C_2$–$C_5$-alkynyl, $C_1$–$C_5$-alkoxy or $C_2$–$C_5$-alkenoxy, $R^2$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl, $R^3$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl, $R^4$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl, or the moiety represented below by P, Q, S or T.

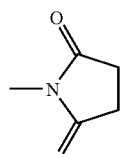

(P)

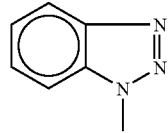

(Q)

(S)

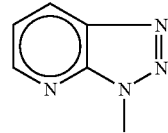

-continued (T)
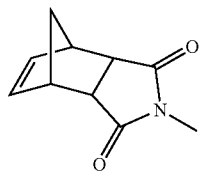

In another aspect the present invention provides novel intermediate compounds represented by a compound of formula 3, Formula 3
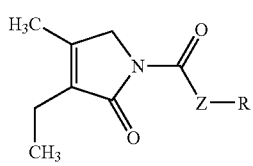

wherein,

Z is O, S or NY, wherein Y is $C_1$–$C_5$-alkyl, $C_1$–$C_5$-haloalkyl, aryl or aralkyl, and R is aryl or heteroaryl, where aryl or hetroaryl radical is unsubstituted or substituted by one or more radicals from the group consisting of nitro, halogen, cyano, azido, haloalkyl, CO—$R^1$, $SR^2$, SO—$R^3$ and $SO_2$—$R^4$, $R^1$ is H, $C_1$–$C_5$-alkyl, $C_2$–$C_5$-alkenyl, $C_2$–$C_5$-alkynyl, $C_1$–$C_5$-alkoxy or $C_2$–$C_5$-alkenoxy, $R^2$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl, $R^3$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl, $R^4$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl, or the moiety represented below by P, Q, S or T.

(P)
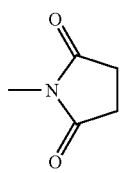

(Q)
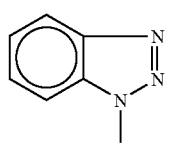

(S)
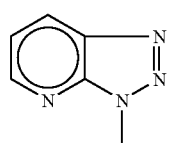

-continued (T)
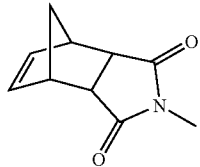

The present invention also provides a novel process for preparation of compound of formula 3, comprising reacting 3-Ethyl-4-methyl-3-pyrrolidin-2-one with a compound of formula 2, Formula 2
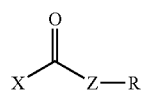

wherein Z and R are as defined above.

In yet another aspect the present invention provides a process for the preparation of a compound of formula 4, Formula 4
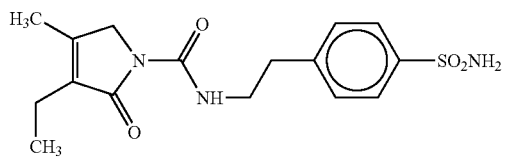

comprising,
a) reacting 3-Ethyl-4-methyl-3-pyrrolidin-2-one with a compound of formula 2, Formula 2
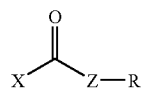

to obtain a compound of formula 3,

Formula 3
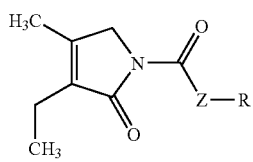

b) reacting the compound of formula 3 with 4-(2-Aminoethyl)benzene sulfonamide to obtain 4-[2-(3-Ethyl-4-methyl-2-carbonyl pyrrolidine amido)ethyl]benzene sulfonamide, a compound of formula 4,
wherein, X is halogen, nitroaryl or haloaryl,
Z is O, S or NY, wherein Y is $C_1$–$C_5$-alkyl, $C_1$–$C_5$-haloalkyl, aryl or aralkyl and R is aryl or heteroaryl, where aryl or hetroaryl radical is unsubstituted or substituted by one or more radicals from the group consisting of nitro, halogen, cyano, azido, haloalkyl, CO—$R^1$, $SR^2$, SO—$R^3$ and $SO_2$—$R^4$, $R^1$ is H, $C_1$–$C_5$-alkyl, $C_2$–$C_5$-alkenyl, $C_2$–$C_5$-alkynyl, $C_1$–$C_5$-alkoxy or $C_2$–$C_5$-alkenoxy, $R^2$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl, $R^3$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl, $R^4$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl, or the moiety represented below by P, Q, S or T.

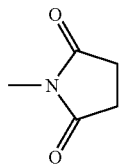
(P)

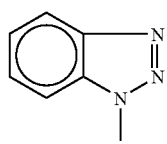
(Q)

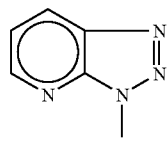
(S)

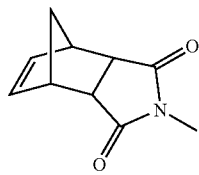
(T)

In still another aspect the present invention provides a process for the preparation of a compound of formula 4,

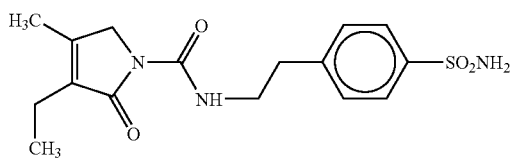
Formula 4 comprising reacting a compound of formula 3

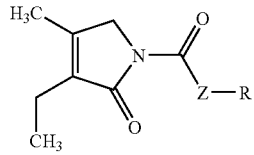
Formula 3 with 4-(2-Aminoethyl)benzene sulfonamide to obtain 4-[2-(3-Ethyl-4-methyl-2-carbonyl pyrrolidine amido)ethyl]benzene sulfonamide, a compound of formula 4, wherein, Z is O, S or NY, wherein Y is $C_1$–$C_5$-alkyl, $C_1$–$C_5$-haloalkyl, aryl or aralkyl and R is aryl or heteroaryl, where aryl or hetroaryl radical is unsubstituted or substituted by one or more radicals from the group consisting of nitro, halogen, cyano, azido, haloalkyl, CO—$R^1$, $SR^2$, SO—$R^3$ and $SO_2$—$R^4$, $R^1$ is H, $C_1$–$C_5$-alkyl, $C_2$–$C_5$-alkenyl, $C_2$–$C_5$-alkynyl, $C_1$–$C_5$-alkoxy or $C_2$–$C_5$-alkenoxy, $R^2$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl, $R^3$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl, $R^4$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl, or the moiety represented below by P, Q, S or T.

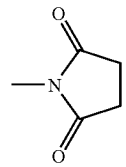
(P)

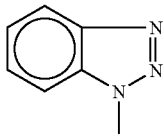
(Q)

(S)

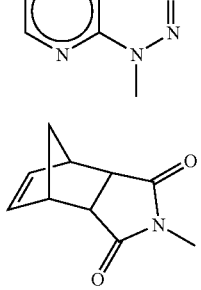
(T)

In one more aspect the present invention provides a process for the preparation of compound of formula 1, comprising reaction of compound of formula 4 with trans-4-methylcyclohexyl isocyanate to obtain the compound of formula 1, characterised in that the compound of formula 4 is prepared by a process comprising reacting a compound of formula 3 with 4-(2-Aminoethyl)benzene sulfonamide to obtain 4-[2-(3-Ethyl-4-methyl-2-carbonyl pyrrolidine amido)ethyl]benzene sulfonamide, a compound of formula 4, wherein Z and R are as defined above.

DETAILED DESCRIPTION OF THE INVENTION

The present invention provides a novel process for the preparation of trans-3-Ethyl 2,5-dihydro-4-methyl-N-[2-[4-[[[[(4-methylcyclohexyl)amino]carbonyl]amino]sulfonyl]phenyl]ethyl]-2-oxo-1H-pyrrole-1-carboxamide.

A preferred embodiment of the process of the present invention is illustrated in Scheme 2, which is presented below.

Scheme 2

I] Preparation of 4-[2-(3-ethyl-4-methyl-2-carbonyl pyrrolidine amido) ethyl]benzene sulfonamide, a compound of formula 4

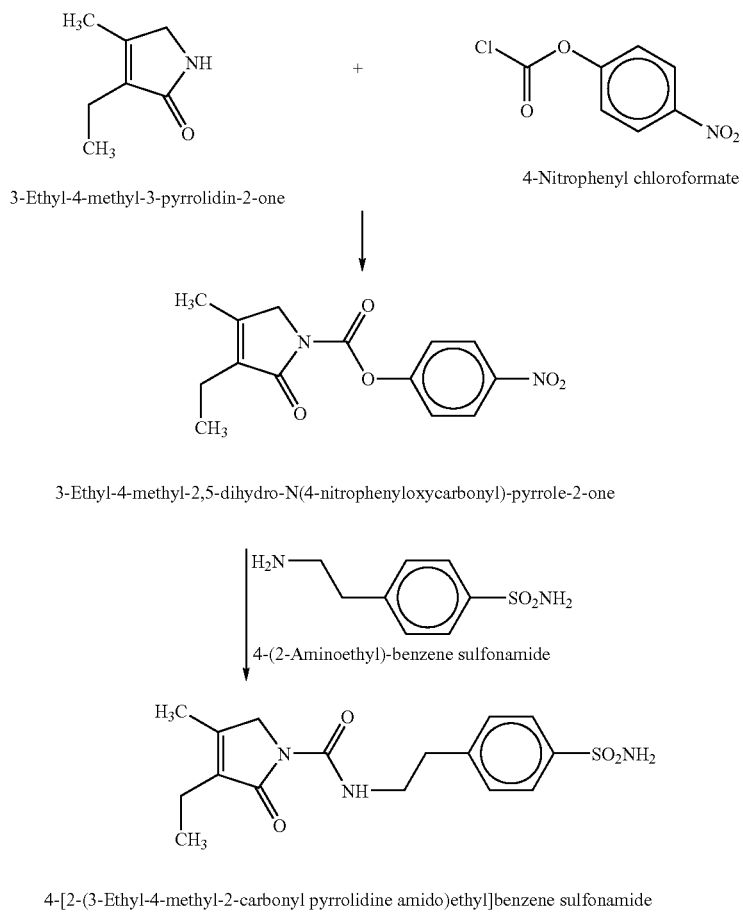

II] Preparation of *trans*-3-ethyl 2,5-dihydro-4-methyl-N-[2-[4-[[[[(4-methylcyclohexyl) amino] carbonyl]amino] sulfonyl]phenyl]ethyl]-2-oxo-1H-pyrrole-1-carboxamide (Glimepiride)

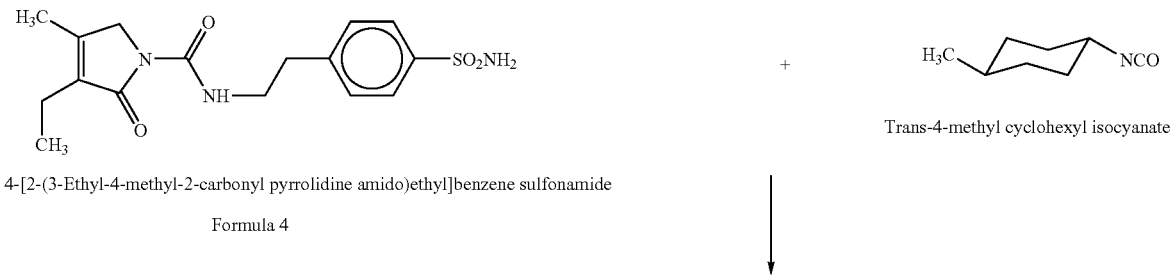

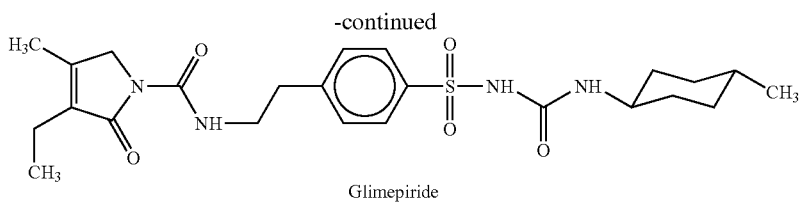

Glimepiride

In formulae 2 and 3, the alkyl, alkoxy, haloalkyl, haloalkoxy, alkylamino and alkylthio radicals and the corresponding unsaturated and/or substituted radicals can be in each case straight-chain or branched in the carbon skeleton. If not stated specifically, the lower carbon skeletons, for example having 1 to 5 carbon atoms or, in the case of unsaturated groups, having 2 to 5 carbon atoms, are preferred for these radicals. Alkyl radicals, including those in the composite meanings, such as alkoxy, haloalkyl and the like, are, for example, methyl, ethyl, n-propyl, i-propyl, n-butyl, i-butyl, t-butyl or pentyl radicals; alkenyl and alkynyl radicals have the meaning of the possible unsaturated radicals corresponding to the alkyl radicals, and alkenyl is, for example, allyl, 1-methylprop-2-en-1-yl, 2-methyl-prop-2-en-1-yl, but-2-en-1-yl, but-3-en-1-yl, 1-methylbut-3-en-1-yl and 1-methylbut-2-en-1-yl; and alkynyl is, for example, propargyl, but-2-yn-1-yl, but-3-yn-1-yl or 1-methylbut-3-yn-1-yl.

Halogen is, for example, F, Cl, Br. Haloalkyl, haloalkenyl, haloalkynyl are alkyl, alkenyl or alkynyl which are partly or completely substituted by halogen, preferably by F, Cl and/or Br, in particular by F, for example, $CF_3$, $CHF_2$; haloalkoxy is, for example, $OCF_3$, $OCHF_2$; corresponding statements apply to haloalkenyl and other radicals substituted by halogen.

Aryl is a mono-, bi- or polycyclic aromatic system, for example phenyl, naphthyl, indanyl, fluorenyl and the like, preferably phenyl substituted with one or more radicals selected from nitro, halo, cyano, 4-trifluoroalkyl, 2,4-bis(trifluoroalkyl) or 2,6-bis(trifluoroalkyl), most preferably 4-nitrophenyl.

Heteroaryl is a mono, bi- or polycyclic aromatic system in which at least one ring contains one or more heteroatoms, for example, pyridyl, pyrimidinyl, pyrazinyl, thienyl, thiazolyl, oxazolyl, furyl, pyrrolyl, imidazolyl, and bicyclic or polycyclic aromatic, for example, quinolinyl, benzoxazolyl and the like. Heteroaryl also includes a heteroaromatic ring, which is preferably 5- or 6-membered and contains 1, 2 or 3 hetero-ring atoms, in particular selected from N, O or S. Heteroaromatic ring can also be benzo-fused.

In substituted radicals, such as substituted aryl, phenyl or substituted heteroaryl radicals, substituents can be, for example, one or more radicals from the group consisting of halogen, alkoxy, haloalkoxy, alkylthio, nitro, cyano, azido, alkoxycarbonyl, alkylcarbonyl, alkylsulfinyl, haloalkylsulfinyl, alkylsulfonyl, haloalkylsulfonyl.

Phenyl is unsubstituted or substituted with one or more than one identical or different radicals preferably from the group consisting of halogen, nitro, haloalkyl and haloalkoxy.

The term nitroaryl means aryl radical substituted with one or more nitro groups.

The term haloaryl means aryl radical substituted with one or more halogen.

The term aralkyl means an alkyl radical in which one hydrogen atom is replaced by an aryl radical, such as benzyl, 2-phenylethyl and the like.

In the process of the present invention, preferably R is aryl or the moiety represented by (P), (Q), (S) or (T), characterised in that aryl is phenyl substituted with one or more radicals selected from nitro, halo, cyano, 4-trifluoroalkyl, 2,4-bis(trifluoroalkyl) or 2,6-bis(trifluoroalkyl).

More preferably, R is aryl selected from phenyl substituted with 4-nitro, 2,4-dinitro, 2,6-dinitro, 4-halo, 2,4-dihalo, 2,6-dihalo, 4-trifluromethyl, 2,4-bis(trifluoromethyl) or 2,6-bis(trifluoromethyl).

In one embodiment of the process of the present invention Z is O and R is selected from the moieties represented by (P), (Q), (S) or (T).

The compound of formula 2, wherein Z is O and R is represented by the moiety (P), (Q), (S) or (T) may be derived from the compounds N-hydroxysuccinimide, 1-hydroxybenzotriazole, 1-hydroxy-7-azabenzotriazole or endo-N-hydroxy-5-norbornene-2,3-dicarboxamide, respectively.

In a preferred embodiment of the process of the present invention, a compound of formula 1 is prepared by the process comprising, a) reacting 3-Ethyl-4-methyl-3-pyrrolidin-2-one with a compound of formula 2, wherein Z is O and R is 4-nitrophenyl, to obtain a compound of formula 3a,

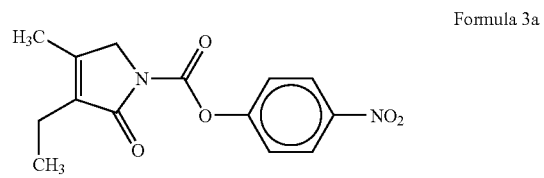

Formula 3a b) reacting the compound of formula 3a with 4-(2-Aminoethyl)benzene sulfonamide to obtain 4-[2-(3-Ethyl-4-methyl-2-carbonyl pyrrolidine amido)ethyl] benzene sulfonamide, a compound of formula 4, c) and further reacting the compound of formula 4 with trans-4-Methylcyclohexyl isocyanate to obtain the compound of formula 1.

The present invention provides novel intermediate compounds of formula 3,

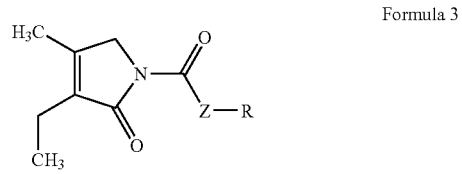

Formula 3 wherein,

Z is O, S or NY, wherein Y is $C_1$–$C_5$-alkyl, $C_1$–$C_5$-haloalkyl, aryl or aralkyl, and R is aryl or heteroaryl, where aryl or hetroaryl radical is unsubstituted or substituted by one or more radicals from the group consisting of nitro, halogen, cyano, azido, haloalkyl, CO—$R^1$, $SR^2$, SO—$R^3$ and $SO_2$—$R^4$, $R^1$ is H, $C_1$–$C_5$-alkyl, $C_2$–$C_5$-alkenyl, $C_2$–$C_5$-alkynyl, $C_1$–$C_5$-alkoxy or $C_2$–$C_5$-alkenoxy, $R^2$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl, $R^3$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl, $R^4$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl, or the moiety represented below by P, Q, S or T.

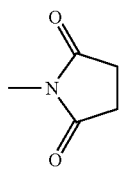
(P)

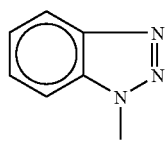
(Q)

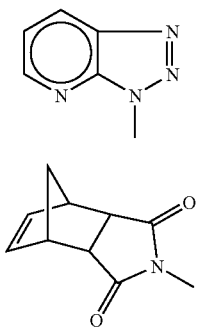
(S)

(T)

The preferred intermediate compounds of formula 3 are the compounds wherein, Z is O and R is aryl or the moiety represented by (P), (Q), (S) or (T), characterised in that aryl is phenyl substituted with one or more radicals selected from nitro, halo, cyano, 4-trifluoroalkyl, 2,4-bis(trifluoroalkyl) or 2,6-bis(trifluoroalkyl).

The more preferred intermediate compounds of formula 3 are the compounds wherein, Z is O and R is selected from phenyl substituted with 4-nitro, 2,4-dinitro, 2,6-dinitro, 4-halo, 2,4-dihalo, 2,6-dihalo, 4-trifluromethyl, 2,4-bis(trifluoromethyl) or 2,6-bis(trifluoromethyl).

In a particularly preferred embodiment the present invention provides a novel intermediate, 3-Ethyl-4-methyl-2,5-dihydro-N-(4-nitrophenyloxy carbonyl)-pyrrole-2-one, a compound of formula 3a.

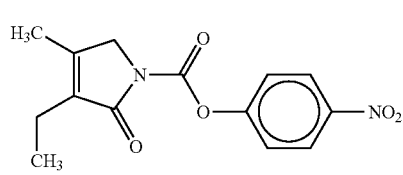
Formula 3a

The compound of formula 3a is preferably prepared by a novel process comprising reacting 3-Ethyl-4-methyl-3-pyrrolidin-2-one with a compound of formula 2, wherein Z is O and R is 4-nitrophenyl.

In a preferred embodiment the present invention provides a process for the preparation of compound of formula 4, comprising a) reacting 3-Ethyl-4-methyl-3-pyrrolidin-2-one with a compound of formula 2, wherein Z is O and R is 4-nitrophenyl, to obtain a compound of formula 3a,

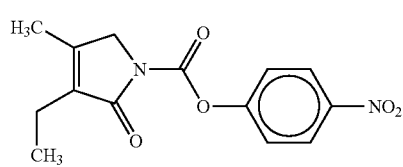
Formula 3a b) reacting the compound of formula 3a with 4-(2-Aminoethyl)benzene sulfonamide to obtain the compound of formula 4.

In another preferred embodiment the present invention provides a process for the preparation of compound of formula 4, comprising reacting the compound of formula 3a with 4-(2-Aminoethyl)benzene sulfonamide to obtain the compound of formula 4.

According to the process of the present invention, the step of the process wherein, 3-Ethyl-4-methyl-3-pyrrolidin-2-one is reacted with a compound of formula 2, to obtain a compound of formula 3, may be carried out in presence of an organic base.

The organic base for carrying out the step of the process, wherein 3-Ethyl-4-methyl-3-pyrrolidin-2-one is reacted with a compound of formula 2, may be selected from group consisting of 4-dimethylaminopyridine; 4-pyrrolidinopyridine; diisopropylethylamine; tetramethylguanidine; 1,8-diazabicyclo[5.4.0]undec-7-ene; 1,5-diazabicyclo[4.3.0]non-5-ene; 2,6-lutidine and picolines. The preferred organic base is 4-dimethylaminopyridine.

Preferably the organic base may be used in a molar equivalent ratio relative to 3-Ethyl-4-methyl-3-pyrrolidin-2-one.

According to the process of the present invention, the reaction of 3-Ethyl-4-methyl-3-pyrrolidin-2-one with a compound of formula 2 to obtain a compound of formula 3, may be carried out in presence of an acid scavenger compound, in addition to the organic base. An acid scavenger compound as used herein is the compound that is capable of neutralizing the acid being generated when 3-Ethyl-4-methyl-3-pyrrolidin-2-one reacts with a compound of formula 2.

The acid scavenger compound may be selected from the group consisting of trialkylamines such as triethylamine, trimethylamine, tri-n-butylamine and the like; pyridine, sodium carbonate, potassium carbonate and the like. The preferred acid scavenger compound is triethylamine. It is also possible to use the organic base such as 4-dimethylaminopyridine in excess, instead of using an acid scavenger compound in addition to the organic base, such that the organic base itself can also act as an acid scavenger compound. But owing to process economics it may be preferable to use an acid scavenger compound such as triethylamine in addition to the organic base for the step of reacting 3-Ethyl-4-methyl-3-pyrrolidin-2-one with a compound of formula 2.

The acid scavenger compound may be used in a molar ratio of 1.5 to 2.2 equivalents, preferably 2 equivalents relative to 3-Ethyl-4-methyl-3-pyrrolidin-2-one.

According to the process of the present invention, the step of the process wherein, 3-Ethyl-4-methyl-3-pyrrolidin-2-one is reacted with a compound of formula 2 may be carried out in a solvent selected from the group consisting of aliphatic or aromatic hydrocarbons, ethers, nitrites, amides and the like. Preferred are hydrocarbon solvents, particularly chlorinated hydrocarbons are preferred, the most preferred solvent is dichloromethane.

According to process of the present invention the step of the process wherein, 3-Ethyl-4-methyl-3-pyrrolidin-2-one is reacted with a compound of formula 2, may be carried out at a temperature between the range of about 0° C. to about 35° C. for about 8 to about 15 hours, preferably about 12 to about 14 hours. In this step of the process, the addition of a compound of formula 2 to 3-Ethyl-4-methyl-3-pyrrolidin-2-one, may be carried out in a controlled manner so as to avoid undue exothermicity. For example, 4-Nitrophenyl chloroformate (a compound of formula 2, wherein X is Cl, Z is O and R is 4-nitrophenyl) may be added in different lots such as 60% of the quantity of 4-Nitrophenyl chloroformate may be added at a temperature range between about 2° C. to about 10° C. and 40% of the quantity of 4-Nitrophenyl chloroformate may be added at temperature range between about 25° C. to about 35° C.

According to the process of the present invention the step 'b' of the process, wherein the compound of formula 3 is reacted with 4-(2-Aminoethyl)benzene sulfonamide to form 4-[2-(3-Ethyl-4-methyl-2-carbonyl pyrrolidine amido)ethyl] benzene sulfonamide, a compound of formula 4, may be carried out in a solvent selected from the group consisting of aliphatic and aromatic hydrocarbons, ketones, nitrites, amides and the like. Preferably the solvent is selected from ketones, nitrites and amides. The most preferred solvent for carrying out the step 'b' of the process is a ketone such as acetone.

According to process of the present invention the step 'b' of the process may be carried out at a temperature between the range of about 35° C. to about 80° C. for about 0.5 to about 20 hours, preferably at about 60° C. for about 0.5 to about 3 hours.

In step 'c' of the process, the compound of formula 4 prepared by the process of the present invention is reacted with trans-4-methylcyclohexyl isocyanate to obtain the compound of formula 1. Step 'c' is known in the art (the '785 patent).

In a particularly preferred embodiment of the process of the present invention, the reaction of 3-Ethyl-4-methyl-3-pyrrolidin-2-one is carried out with a compound of formula 2, wherein X is Cl, Z is O and R is 4-nitrophenyl, to obtain 3-Ethyl-4-methyl-2,5-dihydro-N-(4-nitrophenyloxy carbonyl)-pyrrole-2-one, a compound of formula 3a, having purity greater than 99%.

The compound of formula 3a is reacted with 4(2-Aminoethyl)benzene sulfonamide to obtain 4-[2-(3-Ethyl-4-methyl-2-carbonyl pyrrolidine amido)ethyl]benzene sulfonamide, a compound of formula 4, having purity greater than 99%.

The compound of formula 4 is further reacted with trans-4-methylcyclohexyl isocyanate to obtain a compound of formula 1 having purity greater than 99%.

The following example is given by way of illustration only and not to be construed as limiting.

EXAMPLE 1

Illustrates the Process of the Present Invention a) Preparation of 3-Ethyl-4-methyl-2,5-dihydro-N-(4-nitrophenyloxy carbonyl)-pyrrole-2-one (Compound of Formula 3a)

In a reaction vessel containing dichloromethane (400 ml), 3-Ethyl-4-methyl-3-pyrrolidin-2-one (50 gm, 0.40 moles), followed by 4-Dimethylaminopyridine (49.5 gm, 0.40 moles) and triethylamine (111 ml, 0.80 moles) was added at about 30° C. The reaction is carried out under nitrogen blanket. The reaction mixture was stirred for 10–15 minutes at this temperature to obtain a clear solution. The reaction mixture was cooled to about 0–5° C. using ice-bath.

A solution of 4-Nitrophenyl chloroformate (113 gm, 0.56 moles) in dichloromethane (300 ml) was prepared and gradually added to the above cooled reaction mixture over a period of 1 hour maintaining the temperature at about 5° C. Then the temperature of the reaction mixture was raised to about 30° C. over a period of 1 hour and stirred for 3 hours at this temperature. Maintaining the same temperature, an additional 4-Nitrophenyl chloroformate (19 gm, 0.09 moles) solid, in a single lot was added into the reaction mixture and stirred for 2 hours at about 30° C. In a similar manner, a second lot of 4-Nitrophenyl chloroformate (19 gm, 0.09 moles) solid, was added and the reaction mixture was stirred for 2 hours at about 30° C. A third lot of 4-Nitrophenyl chloroformate (19 gm, 0.09 moles) solid, was added to reaction mixture in a single lot and the reaction mixture was stirred for 5–6 hours at about 30° C.

The reaction mixture was cooled to about 20° C. and cold DM water (500 ml) added to the reaction mixture and stirred for 15 minutes, then it was allowed to settle for 15 minutes. The organic layer was separated and then sequentially washed with (400 ml) of 5% aqueous hydrochloric acid that was cooled to about 20° C., followed by washing with (400 ml) 2.5% aqueous sodium hydroxide solution three times. The organic layer was collected and washed with DM water (400 ml). The organic layer was separated and the solvent was distilled out at about 40° C. with mild vacuum. The resultant syrupy mass was degassed for 1 hour and (200 ml) methanol was added to it at about 30° C. and stirred for 30 minutes. The reaction mixture was cooled to 0–5° C. and stirred for about an hour at this temperature. The resultant product was filtered and washed with (100 ml) methanol two times and sucked to maximum dryness, followed by washing with (100 ml) acetone three times. The resultant product was dried at about 50 to 55° C. in air oven till constant weight to obtain about 85 gm of the product, 3-Ethyl-4-methyl-2,5-dihydro-N-(4-nitrophenyloxy carbonyl)-pyr- b) Preparation of 4[2-(3-Ethyl-4-methyl-2-carbonyl pyrrolidone amido)ethyl]benzene Sulfonamide (Compound of Formula 4)

In a reaction vessel containing acetone (400 ml), 3-Ethyl-4-methyl-2,5-dihydro-N-(4-nitrophenyloxy carbonyl)-pyrrole-2-one (50 gm, 1.0 mole), followed by 4-(2-Aminoethyl) bezene sulfonamide (38 gm, 0.189 mole) was added and stirred for 10–15 minutes. The reaction mixture was refluxed with stirring (internal temperature 55–60° C.) and the temperature was maintained for half an hour. The reaction mixture was allowed to cool to about 30° C. gradually, and then to about 15° C. The reaction mixture was stirred at this temperature for 1 hour. The resultant solid product was filtered and washed four times with chilled acetone (50 ml) and dried at 40–45° C. in air oven till constant weight to obtain about 50 gm of 4[2-(3-Ethyl-4-methyl-2-carbonyl pyrrolidone amido)ethyl]benzene sulfonamide with greater than 99% HPLC (High Performance Liquid Chromatography) purity.

c) Preparation of trans-3-ethyl-2,5-dihydro-4-methyl-N-[2-[4-[[[[(4-methylcyclohexyl)amino]carbonyl]amino]sulfonyl]phenyl]ethyl]-2-oxo-1H-pyrrole-1-carboxamide (Glimepiride)

In a reaction vessel containing (1500 ml) tetrahydrofuran, 4[2-(3-Ethyl-4-methyl-2-carbonyl pyrrolidone amido)ethyl] benzene sulfonamide (100 gm, 0.28 moles) and potassium carbonate (61 gm, 0.44 moles) was added and refluxed at about 60–65° C. for 6 hours.

A solution of trans-4-methylcyclohexyl isocyanate (51.5 gm, 0.37 moles) in toluene (185 ml) was prepared and added to the above reaction mixture and the reaction mixture was refluxed for 4–6 hours, cooled and filtered. To the filtered reaction mass, water (200 ml) was added and the pH was adjusted by addition of aqueous HCl acid to about 6–6.5, followed by pH adjustment to pH of about 8–8.5 with aqueous KOH solution. The solid obtained was filtered and washed with water, followed by methanol to obtain glimepiride (120 gm). The glimepiride was crystallized from 800 ml of 15% w/v methanolic ammonia. The glimepiride with HPLC purity greater than 99.5% was obtained.

Example 2 is provided as a comparative example, which illustrates that when 4[2-(3-Ethyl-4-methyl-2-carbonyl pyrrolidine amido)ethyl]benzene sulfonamide, a compound of formula 4, is prepared according to the process of the product patent (the '785 patent), its HPLC purity is less than the purity obtained when it is prepared by the process of the present invention.

Preparation of 4[2-(3-Ethyl-4-methyl-2-carbonyl pyrrolidone amido)ethyl]benzene sulfonamide (Compound of Formula 4):

3-Ethyl-4-methyl-2,5-dihydro-1H-pyrrole-2-one (15 g) and Phenylethyl isocyanate (19.4 g) were mixed in anhydrous toluene (150 ml) and refluxed for 4 hours, the toluene was distilled off and hexane (75 ml) was added to the reaction mixture at 50° C. and gradually cooled to 0–5° C. to obtain the solid compound, viz. 4[2-(3-Ethyl-4-methyl-2-carbonyl pyrrolidineamido)ethyl]benzene (31.3 gm). It was filtered and washed with hexane.

To a cooled (0–5° C.) solution of chlorosulfonic acid (22.4 ml), 4-[2-(3-Ethyl-4-methyl-2-carbonyl pyrrolidineamido)ethyl]benzene (15 gm) was added in small portions over a period of 1 to 2 hrs. Further it was stirred for 30 minutes at this temperature and then temperature was gradually raised to 30 to 35° C. and stirred for 5 hrs. The reaction mixture was quenched into ice-water, and stirred for 1 hr and filtered to obtain the product 4-[2-(3-Ethyl-4-methyl-2-carbonyl pyrrolidineamido)ethyl]benzene sulfonyl chloride (18.8 g). To a cooled (0–5° C.) solution of concentrated ammonia (100 ml), 4[2-(3-Ethyl-4-methyl-2-carbonyl pyrrolidineamido)ethyl]benzene sulfonyl chloride (10 gm) was added in small portions over 30 minutes. The reaction mixture was stirred at this temperature for 30 minutes and then the reaction mixture was allowed to come to room temperature and then stirred for 5 hrs and filtered and dried to obtain 4-[2-(3-Ethyl-4-methyl-2-carbonyl pyrrolidineamido)ethyl]benzene sulfonamide (7.9 gm) having HPLC purity of about 83 to 85%.

The compound 4-[2-(3-Ethyl-4-methyl-2-carbonyl pyrrolidineamido)ethyl]benzene sulfonamide was purified further from a variety of organic solvents like ester, ketone ethers, alcohol, aromatic, aliphatic or chlorinated hydrocarbons under different conditions, however the purity did not exceed 95% as indicated by HPLC.

What is claimed is:

1. A process for the preparation of trans-3-Ethyl-2,5-dihydro-4-methyl-N-[2-[4-[[[[(4-methylcyclohexyl)amino]carbonyl]amino]sulfonyl]phenyl]ethyl]-2-oxo-1H-pyrrole-1-carboxamide, a compound of the formula 1,

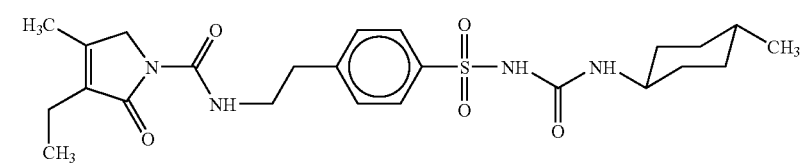

Formula 1 comprising, a) reacting 3-Ethyl-4-methyl-3-pyrrolidin-2-one with a compound of formula 2,

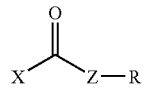

Formula 2 to obtain a compound of formula 3,

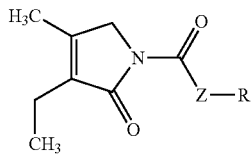

Formula 3 b) reacting a compound of formula 3 with 4-(2-Amino-ethyl)benzene sulfonamide to obtain 4-[2-(3-Ethyl-4-methyl-2-carbonyl pyrrolidine amido)ethyl]benzene sulfonamide, a compound of formula 4,

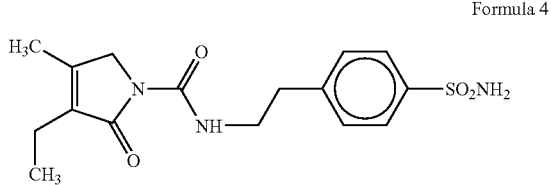

Formula 4 c) and further reacting the compound of formula 4 with trans-4-methylcyclohexyl isocyanate to obtain the compound of formula 1,
wherein,
X is halogen, nitroaryl or haloaryl,
Z is O, and
R is aryl, where aryl radical is unsubstituted or substituted by one or more radicals from the group consisting of nitro, halogen, cyano, azido, haloalkyl, CO—$R^1$, $SR^2$, SO—$R^3$ and $SO_2$—$R^4$,
$R^1$ is H, $C_1$–$C_5$-alkyl, $C_2$–$C_5$-alkenyl, $C_2$–$C_5$-alkynyl, $C_1$–$C_5$-alkoxy or $C_2$–$C_5$-alkenoxy,
$R^2$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl,
$R^3$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl,
$R^4$ is $C_1$–$C_5$-alkyl, $C_2$–$C_5$alkenyl, $C_2$–$C_5$-alkynyl, $C_1$–$C_5$-haloalkyl or $C_2$–$C_5$-haloalkenyl.

2. A process for the preparation of a compound of formula 3,

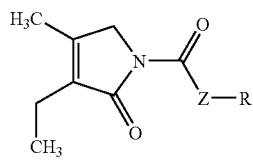

Formula 3 comprising reacting 3-Ethyl-4-methyl-3-pyrrolidin-2-one with a compound of formula 2,

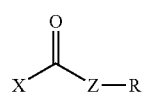

Formula 2 wherein,
X is halogen, nitroaryl or haloaryl
Z is O, and
R is aryl where aryl radical is unsubstituted or substituted by one or more radicals from the group consisting of nitro, halogen, cyano, azido, haloalkyl, CO—$R^1$, $SR^2$, SO—$R^3$ and $SO_2$—$R^4$,
$R^1$ is H, $C_1$–$C_5$-alkyl, $C_2$–$C_5$-alkenyl, $C_2$–$C_5$-alkynyl, $C_1$–$C_5$-alkoxy or $C_2$–$C_5$-alkenoxy,
$R^2$ is $C_1$–$C_5$-alkyl, $C_2$–$C_5$-alkenyl, $C_2$–$C_5$-alkynyl $C_1$–$C_5$-haloalkyl or $C_2$–$C_5$-haloalkenyl,
$R^3$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl,
$R^4$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl.

3. The process as claimed in claim 1 wherein the reaction of 3-Ethyl-4-methyl-3-pyrrolidin-2-one with a compound of formula 2, is carried out in presence of an
organic base and optionally an acid scavenger compound.

4. The process as claimed in claim 1 comprising,
a) reacting 3-Ethyl-4-methyl-3-pyrrolidin-2-one with a compound of formula 2, wherein Z is O and R is 4-nitrophenyl, to obtain a compound of formula 3a,

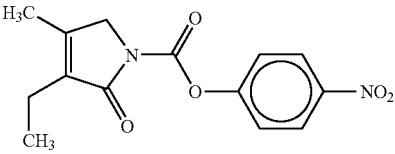

Formula 3a b) reacting the compound of formula 3a with 4-(2-Aminoethyl)benzene sulfonamide to obtain 4-[2-(3-Ethyl-4-methyl-2-carbonyl pyrrolidine amido)ethyl] benzene sulfonamide, a compound of formula 4,
c) and further reacting the compound of formula 4 with trans-4-methylcyclohexyl isocyanate to obtain the compound of formula 1.

5. The process as claimed in claim 3 wherein the organic base is selected from the group consisting of 4-dimethylaminopyridine; 4-pyrrolidinopyridine; diisopropylethylamine, tetramethylguanidine; 1,8-diazabicyclo[5.4.0]undec-7-ene; 1.5-diazabicyclo [4.3.0]non-5-ene; 2,6-lutidine and picolines.

6. The process as claimed in claim 3 wherein the acid scavenger compound is selected from the group consisting of trialkylamines, pyridine, sodium carbonate and potassium carbonate.

7. The process as claimed in claim 3 wherein the organic base is 4-dimethylaminopyridine and the acid scavenger compound is triethylamine.

8. The process as claimed in claim 1 wherein the reaction of 3-Ethyl-4-methyl-3-pyrrolidin-2-one with a compound of formula 2 is carried out in presence of a solvent selected from the group consisting of aliphatic or aromatic hydrocarbons ethers, nitrites and amides.

9. The process as claimed in claim 1 wherein the reaction of 3-Ethyl-4-methyl-3-pyrrolidin-2-one with a compound of formula 2 is carried out in a chlorinated hydrocarbon solvent.

10. The process as claimed in claim 1 wherein the reaction of 3-Ethyl-4-methyl-3-pyrrolidin-2-one with a compound of formula 2 is carried out at a temperature between the range of about 0° C. to about 35° C. for about 8 to about 15 hours.

11. The process as claimed in claim 4 wherein a compound of formula 3a is obtained in a purity of greater than 99%.

12. The process as claimed in claim 4 wherein, a compound of formula 4 is obtained in a purity of greater than 99%.

13. The process as claimed in claim 4 wherein, a compound of formula 1 is obtained in a purity of greater than 99%.

14. The intermediate compound of formula 3,

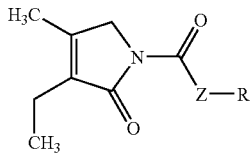

Formula 3 wherein,
Z is O, and
R is aryl where aryl radical is unsubstituted or substituted by one or more radicals from the group consisting of nitro, halogen, cyano, azido, haloalkyl, CO—$R^1$, $SR^2$, SO—$R^3$ and $SO_2$—$R^4$,
$R^1$ is H, $C_1$–$C_5$-alkyl, $C_2$–$C_5$-alkenyl, $C_2$–$C_5$-alkynyl, $C_1$–$C_5$-alkoxy or $C_2$–$C_5$-alkenoxy,
$R^2$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl,
$R^3$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl,
$R^4$ is $C_1$–$C_5$-alkyl, $C_2$–$C_5$-alkenyl, $C_2$–$C_5$-alkynyl, $C_1$–$C_5$-haloalkyl or $C_2$–$C_5$-haloalkenyl.

15. The intermediate compound of formula 3, as claimed in claim 14 wherein Z is O and R is aryl characterised in that aryl is phenyl substituted with one or more radicals selected from nitro, halo, cyano, 4-trifluoroalkyl, 2,4-bis(trifluoroalkyl) or 2,6-bis(trifluoroalkyl).

16. The intermediate compound of formula 3, as claimed in claim 14, wherein Z is O and R is selected from phenyl substituted with 4-nitro, 2,4-dinitro, 2,6-dinitro, 4-halo, 2,4-dihalo, 2,6-dihalo, 4-trifluromethyl, 2,4-bis(trifluoromethyl) or 2,6-bis(trifluoromethyl).

17. The intermediate compound of formula 3a:

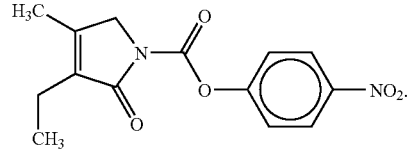

Formula 3a

18. The compound as claimed in claim 17 having a purity greater than 99%.

* * * * *